United States Patent [19]

LaGrandeur et al.

[11] Patent Number: 5,629,290

[45] Date of Patent: May 13, 1997

[54] CYCLIC PEPTIDE ANTIFUNGAL AGENTS

[75] Inventors: Lisa M. H. LaGrandeur, Tucson, Ariz.; Michael J. Rodriguez; Mark J. Zweifel, both of Indianapolis, Ind.

[73] Assignee: Eli Lilly and Company, Indianapolis, Ind.

[21] Appl. No.: 611,611

[22] Filed: Mar. 8, 1996

Related U.S. Application Data

[63] Continuation of Ser. No. 451,705, May 26, 1995.

[51] Int. Cl.⁶ ............................. A61K 38/12; C07K 5/12
[52] U.S. Cl. ......................... 514/11; 424/93.5; 514/9; 500/17
[58] Field of Search ................. 500/317; 424/925; 514/9, 11

[56] References Cited

U.S. PATENT DOCUMENTS

| | | | |
|---|---|---|---|
| 4,293,488 | 10/1981 | Debono | 530/317 |
| 4,293,489 | 10/1981 | Debono | 530/317 |
| 4,320,052 | 3/1982 | Abbott et al. | 530/317 |
| 5,166,135 | 11/1992 | Schmatz | 514/11 |

FOREIGN PATENT DOCUMENTS

| | | |
|---|---|---|
| 359529 | 3/1990 | European Pat. Off. . |
| 447186 | 9/1991 | European Pat. Off. . |
| 448343 | 9/1991 | European Pat. Off. . |
| 448353 | 9/1991 | European Pat. Off. . |
| 448354 | 9/1991 | European Pat. Off. . |
| 448355 | 9/1991 | European Pat. Off. . |
| 448356 | 9/1991 | European Pat. Off. . |
| 462531 | 12/1991 | European Pat. Off. . |
| 503960 | 9/1992 | European Pat. Off. . |
| 525889 | 2/1993 | European Pat. Off. . |
| 561639 | 9/1993 | European Pat. Off. . |
| 2241956 | 9/1991 | United Kingdom . |
| 2242194 | 9/1991 | United Kingdom . |

Primary Examiner—Howard E. Schain
Attorney, Agent, or Firm—Janet T. McClain

[57] ABSTRACT

Provided are pharmaceutical formulations, and methods of inhibiting fungal and parasitic activity using a compound of formula I

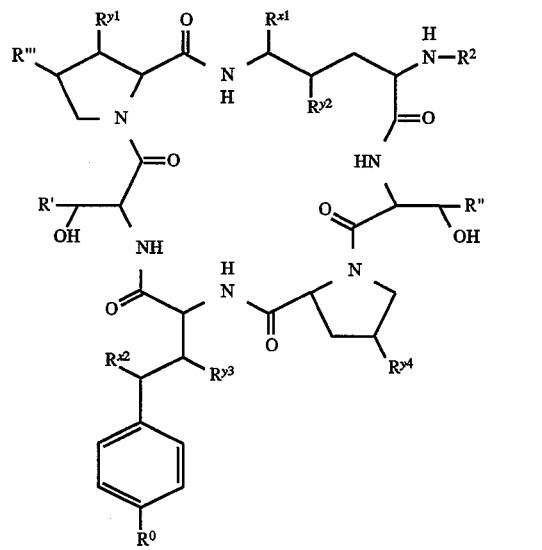

where:

R', R", R''', $R^{x1}$, $R^{x2}$, $R^{y1}$, $R^{y2}$, $R^{y3}$, $R^{y4}$, and $R^o$ are as defined hereinabove; and $R^2$ is

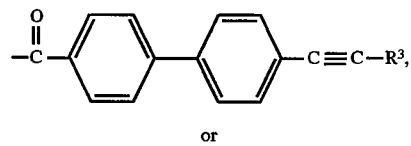

or

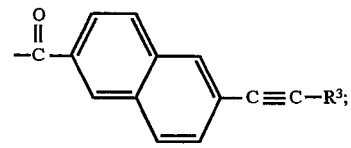

$R^3$ is

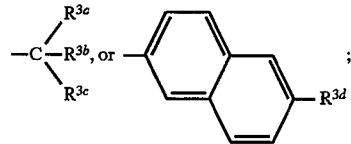

$R^{3a}$ is $C_1$–$C_6$ alkyl or $C_1$–$C_6$ alkoxy;
$R^{3b}$ and $R^{3c}$ are independently phenyl or naphthyl;
$R^{3d}$ is $C_1$–$C_{12}$ alkyl, $C_1$–$C_{12}$ alkoxy or —O —$(CH_2)_m$— [O—$(CH_2)_n$]$_p$—O—($C_1$–$C_{12}$ alkyl);
m is 2, 3 or 4;
n is 2, 3 or 4;
p is 0 or 1;
or a pharmaceutically acceptable salt thereof.

36 Claims, No Drawings

CYCLIC PEPTIDE ANTIFUNGAL AGENTS

This application is a continuation of application Ser. No. 08/451,705, filed on May 26, 1995.

BACKGROUND OF THE INVENTION

This invention relates to semi-synthetic cyclic peptide compounds which are useful as antifungal and antiparasitic agents and which have improved stability and water solubility. In particular, it relates to derivatives of the echinocandin class of cyclic peptides, to methods for treating fungal and parasitic infections, and to formulations useful in the methods.

The compounds provided this invention are semi-synthetic compounds derived from cyclic peptides which are produced by culturing various microorganisms. A number of cyclic peptides are known in the art including echinocandin B (A30912A), aculeacin, mulundocandin, sporiofungin, L-671,329, and S31794/F1.

In general, these cyclic peptides may be structurally characterized as a cyclic hexapeptide core (or nucleus) with an acylated amino group on one of the core amino acids. The amino group is typically acylated with a fatty acid group forming a side chain off the nucleus. For example, echinocandin B has a linoleoyl side chain while aculeacin has a palmitoyl side chain.

The fatty acid side chains may be removed from the cyclic peptide core to provide an amino nucleus (for example, a compound of formula I, below, where $R^2$ is hydrogen). The amino group may then be re-acylated to provide semi-synthetic compounds such as those claimed in the present application.

The echinocandin B nucleus has been re-acylated with certain non-naturally occurring side chain moieties to provide a number of antifungal agents (see, Debono, U.S. Pat. No. 4,293,489. Among such antifungal agents is cilofungin which is represented by a compound of formula IA where R', R" and R''' are methyl, $R^{x1}$, $R^{x2}$, $R^{y1}$, $R^{y2}$, $R^{y3}$, $R^{y4}$ and $R^0$ is hydroxy and $R^2$ is p-(octyloxy)benzoyl.

SUMMARY OF THE INVENTION

The present invention provides a compound of formula I

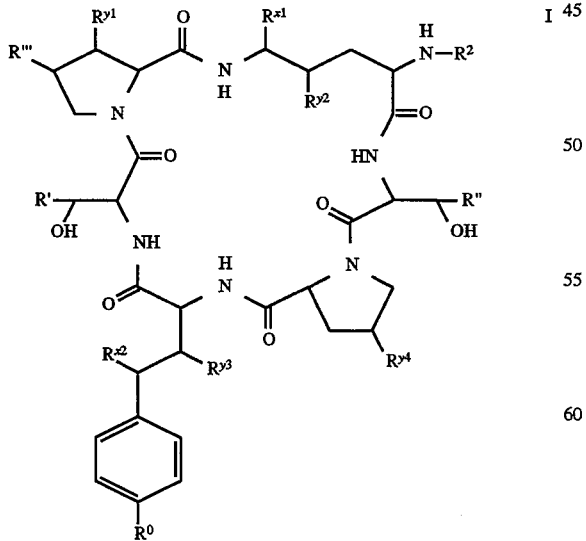

wherein:

R' is hydrogen, methyl or —CH$_2$C(O)NH$_2$;

R" and R''' are independently methyl or hydrogen;

$R^{x1}$ is hydrogen, hydroxy or —O—R;

R is $C_1$–$C_6$ alkyl, benzyl, —(CH$_2$)$_2$Si(CH$_3$)$_3$, —CH$_2$CHOHCH$_2$OH, —CH$_2$CH=CH$_2$, —(CH$_2$)$_a$COOH, —(CH$_2$)$_b$NR$^{z1}$R$^{z2}$, —(CH$_2$)$_c$POR$^{z3}$R$^{z4}$ or —[(CH$_2$)$_2$O]$_d$—(C$_1$–C$_6$) alkyl;

a, b and c are independently 1, 2, 3, 4, 5 or 6;

$R^{z1}$ and $R^{z2}$ are independently hydrogen, $C_1$–$C_6$alkyl, or $R^{z1}$ and $R^{z2}$ combine to form —CH$_2$(CH$_2$)$_e$CH$_2$—;

$R^{z3}$ and $R^{z4}$ are independently hydroxy or $C_1$–$C_6$ alkoxy;

d is 1 or 2;

e is 1, 2 or 3;

$R^{x2}$, $R^{y1}$, $R^{y2}$, $R^{y3}$ and $R^{y4}$ are independently hydroxy or hydrogen;

$R^0$ is hydroxy, —OP(O)(OH)$_2$ or a group of the formulae:

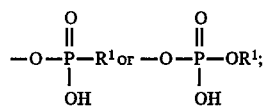

$R^1$ is $C_1$–$C_6$ alkyl, phenyl, p-halo-phenyl, p-nitrophenyl, benzyl, p-halo-benzyl or p-nitro-benzyl;

$R^2$ is

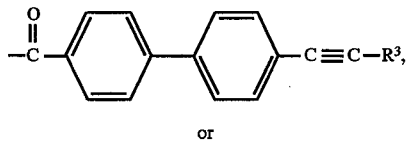

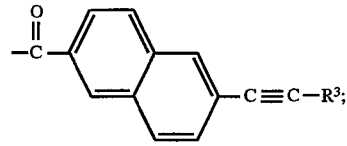

$R^3$ is

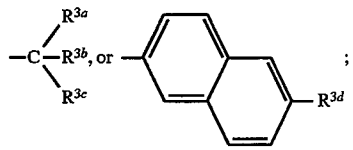

$R^{3a}$ is $C_1$–$C_6$ alkyl or $C_1$–$C_6$ alkoxy;

$R^{3b}$ and $R^{3c}$ are independently phenyl or naphthyl;

$R^{3d}$ is $C_1$–$C_{12}$ alkyl, $C_1$–$C_{12}$ alkoxy or —O—(CH$_2$)$_m$—[O—(CH$_2$)$_n$]$_p$—O—(C$_1$–C$_{12}$ alkyl);

m is 2, 3 or 4;

n is 2, 3 or 4;

p is 0 or 1;

or a pharmaceutically acceptable salt thereof.

Also provided are pharmaceutical formulations, methods for inhibiting parasitic or fungal activity and methods of treating fungal or parasitic infections which employ the compounds of the invention.

DETAILED DESCRIPTION

As used herein, the term "$C_1$–$C_{12}$ alkyl" refers to a straight or branched alkyl chain having from one to twelve carbon atoms. Typical $C_1$–$C_{12}$ alkyl groups include methyl, ethyl, propyl, isopropyl, butyl, sec-butyl, t-butyl, pentyl, 5-methylpentyl, hexyl, heptyl, 3,3-dimethylheptyl, octyl, 2-methyl-octyl, nonyl, decyl, undecyl, dodecyl and the like. The term "$C_1-C_{12}$ alkyl" includes within its definition the terms "$C_1-C_6$ alkyl" and "$C_1-C_4$ alkyl."

The term "halo" refers to chloro, fluoro, bromo or iodo.

The term "$C_1-C_{12}$ alkylthio" refers to a straight or branched alkyl chain having from one to twelve carbon atoms attached to a sulfur atom. Typical $C_1-C_{12}$ alkylthio groups include methylthio, ethylthio, propylthio, isopropylthio, butylthio, 3-methyl-heptylthio, octylthio, 5,5-dimethyl-hexylthio and the like.

The term "$C_1-C_{12}$ alkoxy" refers to a straight or branched alkyl chain having from one to twelve carbon atoms attached to an oxygen atom. Typical $C_1-C_{12}$ alkoxy groups include methoxy, ethoxy, propoxy, butoxy, sec-butoxy, pentoxy, 5-methyl-hexoxy, heptoxy, octyloxy, decyloxy dodecyloxy and the like. The term "$C_1-C_{12}$ alkyl" includes within its definition the terms "$C_1-C_6$ alkoxy" and "$C_1-C_4$ alkoxy."

The term "hydroxy protecting group" refers to a substituent of an hydroxy group that is commonly employed to block or protect the hydroxy functionality while reactions are carried out on other functional groups on the compound. Examples of such hydroxy protecting groups include tetrahydropyranyl, 2-methoxyprop-2-yl, 1-ethoxyeth-1-yl, methoxymethyl, β-methoxyethoxymethyl, methylthiomethyl, t-butyl, t-amyl, trityl, 4-methoxytrityl, 4,4'-dimethoxytrityl, 4,4',4"-trimethoxytrityl, benzyl, allyl, trimethylsilyl, trimethylsilylethyl, (t-butyl)dimehylsilyl, and 2,2,2-trichloroethoxycarbonyl and the like. The species of hydroxy protecting group is not critical so long as the derivatized hydroxy group is stable to the conditions of the subsequent reaction(s) and can be removed at the appropriate point without disrupting the remainder of the molecule. A preferred hydroxy protecting group is trimethylsilylethyl. Further examples of hydroxy protecting groups are described in T. W. Greene, "Protective Groups in Organic Synthesis," John Wiley and Sons, New York, N.Y., (2nd ed., 1991) chapters 2 and 3. The term "protected hydroxy" refers to a hydroxy group bonded to one of the above hydroxy protecting groups.

The term "amino protecting group" as used in the specification refers to substituents of the amino group commonly employed to block or protect the amino functionality while reacting other functional groups on the compound. Examples of such amino protecting groups include formyl, trityl, phthalimido, trichloroacetyl, chloroacetyl, bromoacetyl, iodoacetyl groups, or urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, t-butoxycarbonyl, 2-(4-xenyl) isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)-prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl) ethoxycarbonyl, 2-(methylsulfonyl)ethoxycarbonyl, 2-(triphenylphosphino)-ethoxycarbonyl, fluorenylmethoxy-carbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy) benzyloxycarbonyl, isobornyloxycarbonyl, 1-piperidyloxycarbonyl and the like; benzoylmethylsulfonyl, 2-nitrophenylsulfenyl, diphenylphosphine oxide and like amino protecting groups. The species of amino protecting group employed is not critical so long as the derivatized amino group is stable to the condition of subsequent reaction(s) on other positions of the intermediate molecule and can be selectively removed at the appropriate point without disrupting the remainder of the molecule including any other amino protecting group(s). Preferred amino protecting groups are t-butoxycarbonyl (t-Boc), allyloxycarbonyl and benzyloxycarbonyl (CbZ). Further examples of groups referred to by the above terms are described by J. W. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and sons, New York, N.Y., 1981, Chapter 7.

The term "inhibiting", i.e. a method of inhibiting parasitic or fungal activity, includes stopping, retarding or prophylactically hindering or preventing the growth or any attending characteristics and results from the existence of a parasite or fungus.

The term "contacting", i.e. contacting a compound of the invention with a parasite or fungus, includes a union or junction, or apparent touching or mutual tangency of a compound of the invention with a parasite or fungus. However, the term does not imply any further limitations to the process, such as by mechanism of inhibition, and the methods are defined to encompass the spirit of the invention, which is to inhibit parasitic and fungal activity by the action of the compounds and their inherent antiparasitic and antifungal properties, or in other words, the compounds, used in the claimed methods are the causative agent for such inhibition.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a mineral or organic acid or an inorganic base. Such salts are known as acid addition and base addition salts.

Acids commonly employed to form acid addition salts are mineral acids such as hydrochloric acid, hydrobromic acid, hydroiodic acid, sulfuric acid, phosphoric acid and the like, and organic acids such as p-toluenesulfonic, methanesulfonic acid, oxalic acid, p-bromophenylsulfonic acid, carbonic acid, succinic acid citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

Preferred compounds of this invention are those compounds of formula I where:

R', R" and R'" are each methyl;
$R^{y1}$, $R^{y2}$, $R^{y3}$ and $R^{y4}$ are each hydroxy;
$R^{x1}$ is hydrogen, hydroxy or —O—R;
R is methyl, benzyl, —CH$_2$CHOHCH$_2$OH, —(CH$_2$)$_b$NR$^{z1}$R$^{z2}$ or —(CH$_2$)$_2$POR$^{z3}$R$^{z4}$;
b is 2, 3, 4, 5 or 6;
$R^{z1}$ and $R^{z2}$ are independently hydrogen, or C$_1$–C$_4$ alkyl;
$R^{z3}$ and $R^{z4}$ are independently hydroxy or methoxy;
$R^{x2}$ is hydrogen or hydroxy;
$R^0$ is hydroxy or a group of the formulae:

$$-O-\underset{\underset{OH}{|}}{\overset{\overset{O}{\|}}{P}}-R^1 \quad \text{or} \quad -O-\underset{\underset{OH}{|}}{\overset{\overset{O}{\|}}{P}}-OR^1;$$

R$^1$ is methyl;
or a pharmaceutically acceptable salt thereof.

Of these preferred compounds, more preferred are those compounds of formula I where:

R$^2$ is

—C(=O)—C$_6$H$_4$—C$_6$H$_4$—C≡C—R$^3$;

R$^3$ is

—C(R$^{3a}$)(R$^{3b}$)(R$^{3c}$);

$R^{3a}$ is methyl or methoxy; and
$R^{3b}$ and $R^{3c}$ are each phenyl;
or a pharmaceutically acceptable salt thereof.

Of these more preferred compounds, especially preferred are those compounds of formula I where:

R$^2$ is

—C(=O)—(naphthyl)—C≡C—R$^3$;

R$^3$ is

—(naphthyl)—R$^{3d}$;

$R^{3d}$ is C$_1$–C$_{12}$ alkoxy or —O—(CH$_2$)$_m$—[O—(CH$_2$)$_n$]$_p$—O—(C$_1$–C$_{12}$ alkyl);
m is 2;
n is 2; and
p is 0 or 1;

or a pharmaceutically acceptable salt thereof.

Of the preferred compounds, the most preferred are those compounds where:

$R^{x1}$ is hydroxy, $R^{x2}$ is hydroxy, $R^0$ is hydroxy, and $R^{3a}$ is methyl; and $R^{x1}$ is hydroxy, $R^{x2}$ is hydroxy, $R^0$ is hydroxy, and $R^{3d}$ is —O—(CH$_2$)$_2$—O—(t-butyl);

or a pharmaceutically acceptable salt thereof.

The compounds of formula I may be prepared according to Reaction Scheme I, as follows.

Reaction Scheme I (IA)

[structure of cyclic peptide with substituents R''', R$^{y1}$, R$^{x1}$, R$^{nat}$, R', R'', R$^{y2}$, R$^{y3}$, R$^{y4}$, R$^{x2}$, R$^0$]

A. deacylate

-continued
Reaction Scheme I

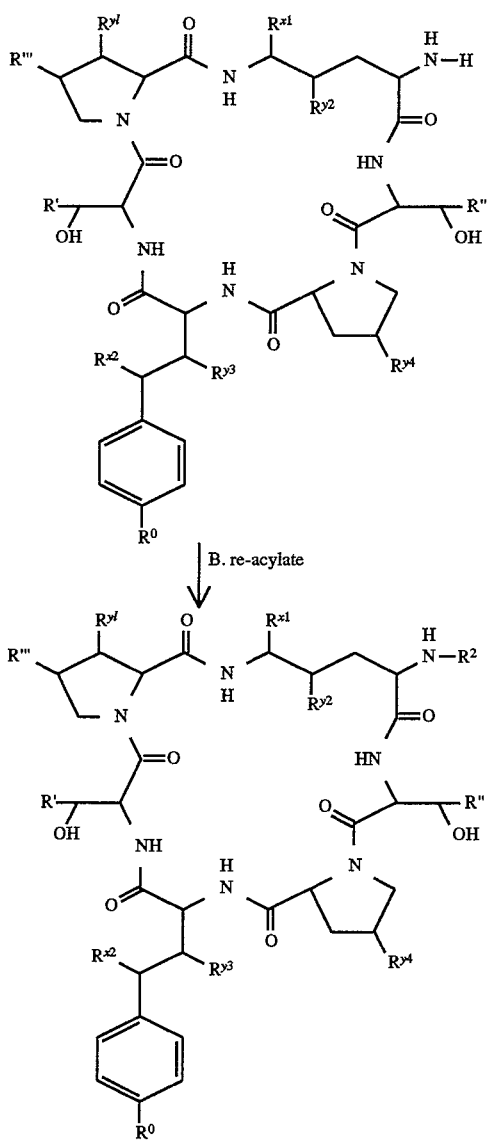

wherein:

R$^{nat}$ is a naturally occurring cyclic peptide sidechain; and R', R", R'", R$^{x1}$, R$^{x2}$, R$^{y1}$, R$^{y2}$, R$^{y3}$, R$^{y4}$, R$^0$ and R$^2$ are as defined above.

Reaction scheme I, above, is accomplished by carrying out reactions A and B, above. Once a reaction is complete, the intermediates compound may be isolated by procedures well-known in the art, for example, the compound may be crystallized or precipitated and then collected by filtration, or the reaction solvent may be removed by extraction, evaporation or decantation. The intermediate compound may be further purified, if desired, by common techniques such as crystallization or precipitation or chromatography over solid supports such as silica gel, alumina and the like, before carrying out the next step of the reaction scheme.

In reaction IA, a naturally occurring cyclic peptide of the formula IA is deacylated using procedures known in the art to provide an amino nucleus of formula IB. This reaction is typically carried out using enzymatic deacylation by exposing the naturally occurring cyclic peptide to a deacylase enzyme. The deacylase enzyme may be obtained from the microorganism *Actinoplanes utahensis* and used substantially as described in U.S. Pat. Nos. 4,293,482 and 4,304,716, herein incorporated by reference. The deacylase enzyme may also be obtained from the Pseudomonas species. Deacylation may be accomplished using whole cells of *Actinoplanes utahensis* or Pseudomonas or the crude or purified enzyme thereof or using an immobilized form of the enzyme. See European Patent Application No. 0 460 882 (Dec. 11, 1991). Examples of naturally occurring cyclic peptides which may be used as starting materials include aculeacin (palmitoyl side chain), tetrahydroechinocandin B (stearoyl side chain), muliundocandin (branched C$_{15}$ side chain), L-671,329 (C$_{16}$ branched side chain), S 31794/F1 (tetradecanoyl side chain), sporiofungin (C$_{15}$ branched side chain), FR901379 (palmitoyl side chain) and the like. A preferred naturally occurring cyclic peptide is echinocandin B (a compound of formula IA where R', R" and R'" are each methyl, R$^{x1}$, R$^{x2}$, R$^{y1}$, R$^{y2}$, R$^{y3}$, R$^{y4}$ and R$^0$ are each hydroxy and R$^2$ is linoleoyl).

In Reaction IB, the amino nucleus of formula IB is re-acylated using procedures known in the art to provide a compound of formula I where R$^2$ is an acyl group as defined hereinabove.

For example, the amino nucleus may be acylated by reaction with an appropriately substituted acyl halide, preferably in the presence of an acid scavenger such as a tertiary amine, such as triethylamine. The reaction is typically carried out at a temperature of from about −20° C. to about 25° C. Typical solvents for this reaction include polar aprotic solvents such as dioxane or dimethylformamide. Solvent choice is not critical so long as the solvent employed is inert to the ongoing reaction and the reactants are sufficiently solubilized to effect the desired reaction.

The amino nucleus may also be acylated by reaction with an appropriately substituted carboxylic acid, in the presence of a coupling agent. Typical coupling agents include dicyclohexylcarbodiimide (DCC), N,N'-carbonyldiimidazole, bis(2-oxo-3-oxazolidinyl)phosphinic chloride (BOP-Cl), N-ethoxycarbonyl-2-ethoxy-1,2-dihydroquinoline (EEDQ), benzotriazol-1-yloxytripyrrolidinophosphonium hexafluorophosphate (PyBOP) and the like.

In addition, the amino nucleus may be acylated with an activated ester of a carboxylic acid such as an ester of a carboxylic acid of the formula R$^2$—COOH and p-nitrophenyl 2,4,5-trichlorophenyl, hydroxybenzotriazole hydrate (HOBT·H$_2$O), pentafluorophenol, N-hydroxysuccinimide and the like. Preferred acylating moieties are the active esters of the carboxylic acid R$^2$—COOH such as 2,4,5-trichlorophenyl ester and benzotriazole ester. The reaction is typically carried out for one to sixty five hours at a temperature from about 0° C. to about 30° C. in an aprotic solvent. The reaction is generally complete after about twenty four to forty eight hours when carried out a temperature of from about 15° C. to about 30° C. Typical solvents for this reaction are tetrahydrofuran and dimethylformamide or a mixture of such solvents. The amino nucleus is generally employed in equimolar proportions relative to the activated ester or with a slight excess of the amino nucleus.

The compounds of formula I where R$^{x1}$ is hydroxy may be reacted with an appropriately substituted alcohol in the presence of an acid to provide a compound of formula I where R$^{x1}$ is —O—R, where R is C$_1$–C$_6$ alkyl, benzyl, —(CH$_2$)$_2$Si (CH$_3$)$_3$, —CH$_2$CH=CH$_2$, —(CH$_2$)$_a$COOH, —(CH$_2$)$_b$NR$^{z1}$R$^{z2}$, —(CH$_2$)$_c$POR$^{z3}$R$^{z4}$ or —[(CH$_2$)$_2$O]$_d$-(C$_1$–C$_6$)alkyl. The reaction is typically carried out in a polar aprotic solvent such as dioxane or dimethylsulfoxide at a temperature of from about 0° C. to about 35° C., preferably at about room temperature. Solvent choice is not critical so long as the solvent employed is inert to the ongoing reaction and the reactants are sufficiently solubilized to effect the desired reaction. Preferred acids include p-toluenesulfonic acid, hydrochloric acid and camphorsulfonic acid.

The compounds of formula I where $R^{x1}$ is —$(CH_2)_b NR^{z1}R^{z2}$ where $R^{z1}$ and $R^{z2}$ are hydrogen may be prepared via a protected compound wherein $R^{x1}$ is —$(CH_2)_b NHR^a$ where $R^a$ is an amino protecting group. The resultant protected compound is then deprotected according to procedures known in the art.

The compounds of formula I where $R^{x1}$ is —$CH_2CHOHCH_2OH$ may be prepared by hydroxylating a compound of formula I where $R^{x1}$ is —$CH_2CH=CH_2$ with osmium tetroxide in the presence of a catalyst at a temperature in the range of from about 0° C. to about 40° C. for about one to twenty four hours in a organic/aqueous solvent mixture, for example dioxane/water. Suitable catalysts include N-methylmorpholine N-oxide (NMO) and the like. Typical solvents suitable for use in this reaction include dimethylformamide, tetrahydrofuran, acetone and dioxane. Solvent choice is not critical so long as the solvent employed is inert to the ongoing reaction and the reactants are sufficiently solubilized to effect the desired reaction. The reaction is preferably conducted at a temperature in the range of from about 20° C. to about 30° C. for about eighteen to twenty four hours.

The compounds of formula I where $R^0$ is hydroxy may be phosphorylated by reaction with an appropriately substituted alkyl or phenyl phosphate to provide a compound of formula I where $R^0$ is —O—P(O)OH—$R^1$ where $R^1$ is $C_1$–$C_6$ alkoxy or phenoxy, or by reaction with an appropriately substituted alkyl or phenyl phosphonic acid to provide a compound of formula I where $R^0$ is —O—P(O)OH—$R^1$ where $R^1$ is $C_1$–$C_6$ alkyl, or an appropriately substituted phenyl or benzyl moiety, to provide a compound of formula I where $R^0$ is a group of the formula —OP(O)OH—$R^1$. The phosphonic acid is typically used in an activated form, for example as a phosphonic halide, preferably a phosphonic chloride. The reaction is carried out in the presence of a base such as lithium trimethylsilanolate (LiOTMS), lithium bis (trimethylsilyl) amide (LHMDS), pyridine and the like. The reaction is typically carried out for up to one hour at a temperature from about −30° C. to about 0° C. in an aprotic solvent such as tetrahydrofuran and dimethylformamide. The reaction is generally complete in about fifteen minutes when carried out under these conditions. The phosphate or phosphonate reactant is generally employed in equimolar proportions to about a one mole excess relative to the amino nucleus in the presence of an equimolar or slight excess of the base. Phosphorylation of an amino nucleus with unprotected aminal hydroxy groups is typically carried out at lower temperatures, for example from about −30° C. to about −15° C.

Alternatively, the aminal hydroxy moieties on the compound of formula I are optionally protected with an hydroxy protecting group using procedures known in the art. For example, the reaction is typically carried out by combining the compound of formula I with a suitable hydroxy protecting group in the presence of a catalyst at a temperature in the range of from about 0° C. to about 40° C. for about one to five hours in a mutual inert solvent. The hydroxy protecting group is generally employed in an amount ranging from about equimolar proportions to about a 100 molar excess relative to the compound of formula I, preferably in a large molar excess. Suitable catalysts include strong acids such as p-toluenesulfonic acid, camphorsulfonic acid (CSA), hydrochloric acid, sulfuric acid, trifluoroacetic acid and the like.

Typical solvents suitable for use in this reaction include any organic solvent such as dioxane. Solvent choice is not critical so long as the solvent employed is inert to the ongoing reaction and the reactants are sufficiently solubilized to effect the desired reaction. The reaction is preferably conducted at a temperature in the range of from about 20° C. to about 30° C. for about two to four hours. The protected compound of formula I is then phosphorylated as described above. The hydroxy protecting group(s) are then removed according to procedures known in the art to provide a phosphorylated compound of formula I. For example, the protecting groups can be removed by reaction with a Lewis acid in a mutual inert organic solvent such as methylene chloride. Examples of Lewis acids include trimethylsilylbromide, boron trifluoride etherate and the like. The reaction is typically carried out at a temperature of from about 0° C. to about 40° C., preferably at a temperature of from about 20° C. to about 30° C. A preferred Lewis acid is boron trifluoride etherate.

The dideoxy compounds of formula I are prepared by removing the benzylic and aminal hydroxy groups ($R^{x2}$ and $R^{x1}$, respectively). The hydroxy groups: may be removed by subjecting a non-dideoxy compound of formula I (where $R^2$ is hydrogen or acyl) to a strong acid and a reducing agent at a temperature of between −5° C. and 70° C., in a suitable solvent. Typical strong acids include trichloroacetic acid, trifluoroacetic acid or borontrifluoride etherate. A preferred strong acid is trifluoroacetic acid. Typical reducing agents include sodium cyanoborohydride or triethylsilane. A preferred reducing agent is triethylsilane. Suitable solvents include methylene chloride, chloroform or acetic acid, preferably methylene chloride. The strong acid should be present in an amount of from 2 to 80 mol per mol of substrate, and the reducing agent should be present in an amount of 2 to 80 mol per mol of substrate. This process affords selective removal of the aminal and benzylic hydroxy groups.

The cyclic peptides used to make the compounds of the present invention may be prepared by fermentation of known microorganisms. For example, the cyclic peptide of formula IB where R', R" and R'" are methyl, and $R^{x1}$, $R^{x2}$, $R^{y1}$, $R^{y2}$, $R^{y3}$, $RY^4$ and $R^0$ are each hydroxy (cyclic nucleus corresponding to A-30912A) may be prepared using the procedure detailed in Abbott et al., U.S. Pat. No. 4,293,482, which is herein incorporated by reference. The cyclic peptide of formula IB where R', R" and R'" are methyl, $R^{x1}$ is hydroxy, $R^{x2}$ is hydrogen, and $R^{y1}$, $R^{y2}$, $R^{y3}$, $RY^4$ and $R^0$ are each hydroxy (cyclic nucleus corresponding to A-30912B) may be prepared using the procedure detailed in Abbott et al., U.S. Pat. No. 4,299,763, which is herein incorporated by reference. Aculeacin may be prepared using the procedure detailed in Mizuno et al., U.S. Pat. No. 3,978,210 which is herein incorporated by reference. The cyclic peptide of formula IB where R' is —$CH_2C(O)NH_2$, R" is methyl, R'" is hydrogen, and $R^{x1}$, $R^{x2}$, $R^{y1}$, $R^{y2}$, $R^{y3}$, $RY^4$ and $R^0$ are each hydroxy may be prepared by deacylating the cyclic peptide prepared using the procedure detailed in Chen et al. U.S. Pat. No. 5,198,421, which is herein incorporated by reference.

The $R^2$—COOH precursor acids are prepared by reacting an appropriately substituted acetylene reactant with a compound of the formula:

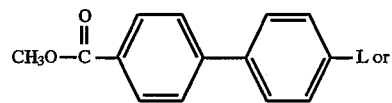

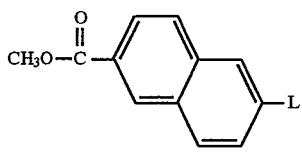

where L is a suitable leaving group such as bromo, iodo, trifluoromethanesulfonate and the like, in the presence of a catalyst or catalysts and preferably in the presence of an acid scavenger in a mutual inert solvent such as acetonitrile. Examples of acid scavengers include triethylamine and pyridine, preferably triethylamine. Preferred catalysts are formed in situ from palladium (II) chloride, triphenylphosphine and copper (I) iodide. The reaction is typically carried out for thirty minutes to twenty one hours at a temperature from about room temperature to the reflux temperature of reaction mixture. The reaction is generally complete after about two to about six hours when carried out at reflux temperature.

The resultant methyl ester is hydrolyzed using procedures known in the art to provide the corresponding carboxylic acid which is then converted to an activated ester, preferably a 2,4,5-trichlorophenyl ester, which is used to acylate the cyclic peptide nucleus as described above. For example, the methyl ester may be hydrolyzed by refluxing it with an excess of sodium hydroxide solution in an alcoholic solvent, preferably methanol and then acidifying the reaction mixture, for example, by the addition of an hydrochloric acid solution. The carboxylic acid may be converted to the corresponding 2,4,5-trichlorophenyl ester by combining the carboxylic acid with 2,4,5-trichlorophenol and a coupling agent such as N,N'-dicyclohexylcarbodiimide (DCC) in a mutual inert solvent such as methylene chloride.

The following Preparations and Examples further describe how to synthesize the compounds of the present invention. The terms melting point, proton nuclear magnetic resonance spectra, mass spectra, infrared spectra, ultraviolet spectra, elemental analysis, high performance liquid chromatography, and thin layer chromatography are abbreviated "m.p.", "NMR", "MS", "IR", "UV", "Analysis", "HPLC", and "TLC", respectively. In addition, the absorption maxima listed for the IR spectra are only those of interest and not all of the maxima observed.

PREPARATION 1

A. 2,2-Diphenyl-propanol

To a cold (0° C.) mixture of 4.3 g (114 mmol) of lithium aluminum hydride in 100 ml of tetrahydrofuran, was added 10.74 g (47 mmol) of 2,2-diphenylpropanoic acid in portions. The resulting reaction mixture was allowed to warm to room temperature. When the reaction was substantially complete, as indicated by thin layer chromatography (TLC), the reaction mixture was diluted with approximately 10 ml of water, 8 ml of 1N sodium hydroxide and diethyl ether and stirred for ninety minutes at 0° C. The reaction mixture was then poured over celite, and washed sequentially with diethyl ether and eluted using a gradient eluent of 5–20% ethyl acetate in hexane. The fractions containing the desired compound were combined and concentrated in vacuo to provide 9.38 g of material.
Yield: 93%.

B. 2,2-Diphenylpropaldehyde

A solution of 4.56 g (21 mmol) of the subtitled compound of Preparation 1A in 50 ml of methylene chloride to a cold (0° C.) mixture of celite and 23.2 g (107 mmol) pyridinium chlorochromate (1:1 w/w) in methylene chloride. The resultant reaction mixture was allowed to react for approximately two hours at 0° C. and then was allowed to warm to room temperature and reacted for an additional two hours. The reaction mixture was diluted with diethyl ether and poured over a silica pad wetted with ether. The desired product was eluted using an eluent of 20% ethyl acetate in hexane. The fractions containing the desired compound were combined and concentrated in vacuo to yield a yellow oil. This oil was purified using reverse phase HPLC (eluent of 80% aqueous acetonitrile, 254 nm) to provide 3.75 g of the desired compound.
Yield: 83%.

C. 1-Bromo-3,3-diphenyl-but-1-ene

To a cold (–78° C.) anhydrous suspension of 6.22 g (14 mmol) of (bromomethyl)triphenylphosphonium bromide in 40 ml of tetrahydrofuran, was added 1.6 g (14 mmol) of potassium t-butoxide in portions. The resultant mixture was allowed to stir for approximately twenty minutes during which time the mixture turned bright yellow. To this mixture, was then added 2 g (9.5 mmol) of the subtitled compound of Preparation 1B in anhydrous tetrahydrofuran and the resultant mixture was allowed to react for approximately five hours. Following the addition of methyl iodide, the reaction mixture was slowly warmed to room temperature and then poured into diethyl ether. The resulting layers were separated and the organic layer was washed sequentially with water and brine and then concentrated in vacuo to provide a residue. This residue was redissolved in diethyl ether and more methyl iodide and water were added. The resulting layers were separated and the organic portion was washed with brine and then concentrated in vacuo to provide crude material. This material was purified using flash chromatography (silica, eluent of 5% ethyl acetate in hexane) to provide 1.31 g of the desired compound.
Yield: 48%.

D. 3,3-Diphenyl-but-1-yne

To a cold (–78° C.) solution of 1.31 g (4.6 mmol) of the subtitled compound of Preparation 1C in 100 ml of anhydrous tetrahydrofuran, was added 4.9 ml (6.8 mmol) of methyl lithium, dropwise. The resultant reacton mixture was reacted for approximately fifteen minutes and then warmed to 0° C. and reacted for an additional 2.75 hours. The reaction was then quenched by the slow addition of water. The resulting mixture was diluted with diethyl ether, the resulting layers were separated and the organic portion was washed sequentially with water and brine, dried over magnesium sulfate, filtered and then concentrated in vacuo to provide a crude material. This material was purified using flash chromatography (silica, eluent of 5% ethyl acetate in hexane) followed by reverse phase HPLC (eluent of 80% aqueous acetonitrile, 254 rim) to provide 0.255 g of the desired compound.
Yield: 27%.

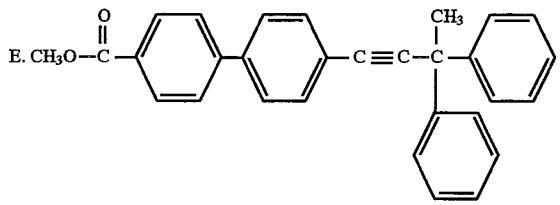

To a solution of 0.255 g (1.2 mmol) of the subtitled compound of Preparation 1D in 7.9 ml of anhydrous acetonitrile, was added (in order) 0.445 g (1.2 mmol) of the subtitled compound of Preparation 5A, 0.250 g (2.5 mmol) of triethylamine, 10.96 mg (0.06 mmol) of palladium (II) chloride, 32.4 mg (0.12 mmol) of triphenylphosphine, 5.9 mg of copper (I) iodide. The resultant reaction mixture was refluxed for approximately twenty one hours and then cooled to room temperature resulting in the formation of a very thick precipitate. The mixture was concentrated to one half volume and filtered. The precipitate was washed with acetonitrile to provide 0.284 g of a shiny grey solid which was used without further purification.
Yield: 56%.

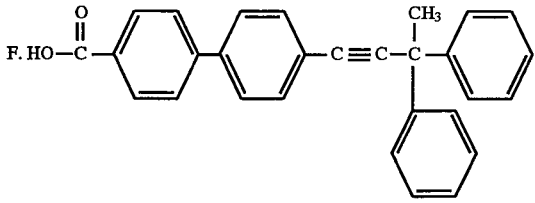

To solution of 0.328 g (0.79 mmol) of the subtitled compound of Preparation 1E in 40 ml of dioxane, was added 2 ml of a 2N sodium hydroxide solution. The resultant reacton mixture was refluxed for approximately 14.5 hours. After cooling the reaction mixture to room temperature, 4 ml of a 1N hydrochloric acid solution was added and the resultant mixture was stirred at room temperature for 2.5 hours. The resultant mixture was then concentrated in vacuo and poured into diethyl ether. The resultant layers were separated and the organic layer was washed sequentially with water and brine, dried over magnesium sulfate, filtered and then concentrated in vacuo to provide 0.463 g of the desired compound which was used without further purification.
Yield: 146% (wet).

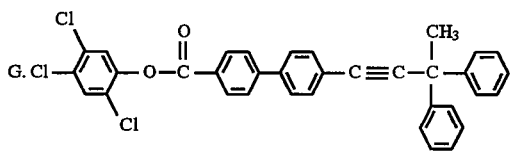

To a suspension containing 0.463 g (1.2 mol) of the compound of Preparation 1F in 100 ml of anhydrous methylene chloride, was added 0.227 g (1.2 mmol) of 2,4,5-trichlorophenol and 0.237 mg (1.28 mmol) dicylcohexylcarbodiimde (DCC). The resultant reaction mixture was allowed to react overnight at room temperature. When the reaction was substantially complete, as indicated by TLC, the reaction mixture was concentrated in vacuo and then mixed with diethyl ether resulting in the formation of fine white crystals. These crystals was dried to provide to provide 195 mg of the desired compound.
Yield: 34%.

PREPARATION 2

A. 1-trimethylsilyl-2,2-diphenyl-3-methoxy-prop-1-yne

To a cold (–78° C.) solution of 10.4 g (106 mmol) of trimethylsilyl-acetylene in 300 ml of anhydrous tetrahydrofuran, was added 66 ml (106 mmol) of n-butyl lithium. After stirring the resultant mixture for approximately fifteen minutes, 4.8 g (318 mmol) benzophenone was added, and the resultant mixture was allowed to react for approximately forty five minutes and then warmed to 0° C. and reacted for an additional two hours. To the resultant solution, was added 19.8 ml (318 mmol) of methyl iodide. After allowing the reaction mixture to react for approximately two hours, an additional 50 ml of methyl iodide mixture was placed in a refrigerator overnight. The reaction mixture was poured into a mixture of diethyl ether and ice. The resultant layers were separated and the organic layer was washed sequentially with water (twice) and brine (twice), dried over sodium sulfate, filtered and concentrated in vacuo to provide the desired compound which was used without further purification.

B. 2,2-diphenyl-3-methoxy-prop-1-yne

To a cold (0° C.): solution of the subtitled compound of Preparation 2A in 400 ml of methanol, was added an excess of potassium carbonate. The resultant reaction mixture was reacted for approximately one hour and then warmed to room temperature and reacted for another 1.25 hours. When the reaction was substantially complete, as indicated by TLC (5% ethyl acetate in hexane), the reaction mixture was poured into a mixture of diethyl ether and ice. The resultant layers were separated and the organic layer was washed sequentially with water (three times) and brine (twice), dried over sodium sulfate, filtered and concentrated in vacuo to provide a yellow oil which was used without further purification.

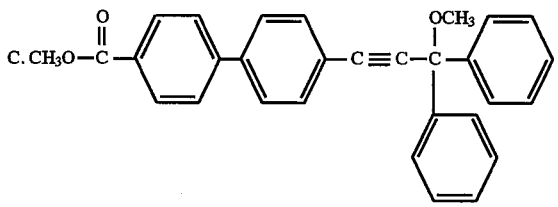

The desired subtitled compound was prepared substantially in accordance with the procedure detailed in Preparation 1E, using 1.0 g (4.5 mmol) of the subtitled compound of Preparation 2B, 1.62 g (4.5 mmol) of the subtitled compound of Preparation 5A, 0.91 g (9.0 mmol) of triethylamine, 0.0399 g (0.22 mmol) of palladium (II) chloride, 0.118 g (0.44 mmol) of triphenylphosphine, 0.021 mg (0.1 mmol) of copper (I) iodide in 29 ml of anhydrous acetonitrile.

Yield: 0.97 g (50%).

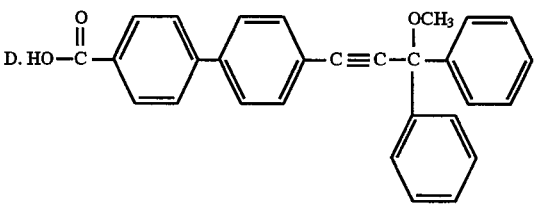

The desired subtitled compound was prepared substantially in accordance with the procedure detailed in Preparation 1F, using 0.97 g of the subtitled compound of Preparation 2C, 4.4 ml of a 2N sodium hydroxide solution in 150 ml of dioxane. After the reaction mixture was complete, as indicated by TLC, the reaction was combined with 8.8 ml of a 1N hydrochloric acid solution.

Yield: 0.87 g (93%).

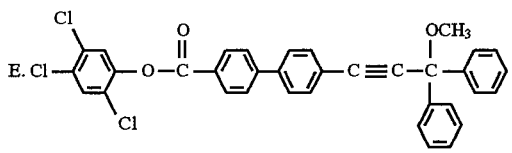

The desired subtitled compound was prepared substantially in accordance with the procedure detailed in Preparation 1G, using 0.87 g (2 mmol) of the compound of Preparation 2D, 0.411 g (2 mmol) of 2,4,5-trichlorophenol and 0.429 (2 mmol) dicylcohexylcarbodiimde (DCC) in 50 ml of anhydrous methylene chloride.
Yield: 1.21 g (97%).

PREPARATION 3

A. O-(toluylsulfonyl)-2-butoxy-ethanol

To a cold (0° C.) solution of 118.18 (1 mol) of 2-butoxy-ethanol in anhydrous pyridine, was added 190.66 g (1 mol) of toluenesulfonylchloride. The resultant reaction mixture was allowed to react for approximately one hour at 0° C., then at room temperature for approximately two hours. When the reaction was substantially complete, as indicated by TLC, the reaction mixture was concentrated in vacuo to provide a residue. This residue was partitioned between diethyl ether and a 1N aqueous hydrochloric acid solution and the organic phase was washed sequentially with a 2N sodium hydroxide solution, a 1N hydrochloric acid solution, water, and brine, and then dried over sodium sulfate, filtered and concentrated in vacuo to provide 200.39 g of a light gold oil.
Yield: 73.6%.
MS(FD): 273 (M).

B. 2-(2-(2-t-butoxy)-ethoxy)-6-bromo-naphthalene

A mixture containing 10.00 g (44.83 mmol) of 6-bromo-2-naphthol, 12.210 g (44.829 mmol) of the compound of Preparation 3A, and 12.392 g (89.66 mmol) of granular potassium carbonate in 130 ml of acetonitrile was refluxed overnight. When the reaction was substantially complete, as indicated by TLC, the reaction mixture was cooled to room temperature and concentrated in vacuo to provide a residue. This residue was redissolved in ethyl acetate and washed sequentially with a 1N hydrochloric acid solution, water, a 2N sodium hydroxide solution, water and brine, and then dried over sodium sulfate, filtered and concentrated in vacuo to provide 13.14 g of an off-white solid.
Yield: 90.7%.
MS(FD): 322, 324 (M).

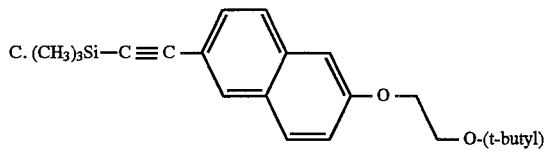

To a solution containing 13.00 g (40.219 mmol) of the compound of Preparation 3B, 5.68 ml (40.219 mmol) of trimethylsilyl-acetylene, and 11.211 ml (80.437 mmol) of triethylamine in 100 ml of acetonitrile, was added 357 mg (2.01 mmol) of palladium (II) chloride, 1.055 g (4.022 mmol) of triphenylphosphine and 169 mg (0.885 mmol) of copper (I) iodide, under nitrogen. The resultant reaction mixture was refluxed for approximately three hours. When the reaction was substantially complete, as indicated by TLC, the reaction mixture was cooled to room temperature and concentrated in vacuo to provide a residue. This residue was redissolved in hexanes and and the resultant mixture was sonicated resulting in the formation of a precipitate. This precipitate was isolated by filtration to provide 7.33 g of a light brown solid.
Yield: 54%.
MS(FD): 340 (M).

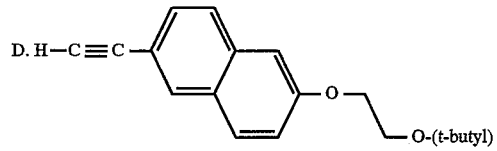

To a solution of 7.3 g (0.021 mol) of the compound of Preparation 3C in 250 ml of a 2:3 methanol/methylene chloride mixture, was added 20 g (0.15 mol) of granular potassium carbonate. The resultant reaction mixture was reacted at room temperature for approximately five hours. When the reaction was substantially complete, as indicated by TLC, the reaction mixture filtered to remove the solid material and then dried in vacuo to provide 5.98 g of a black solid.
Yield: quantitative.
MS(FD): 268 (M).

PREPARATION 4

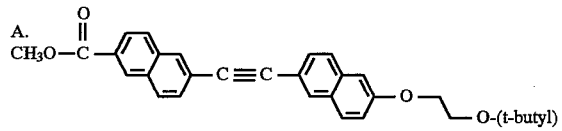

To a mixture containing 1.868 g (5.590 mmol) of 2-(O-trifluoromethylsulfonyl)-6-carbomethoxy naphthalene, 1.500 g (5.590 mmol) of the compound of Preparation 3D, and 1.56 ml (11.179 mmol) of anhydrous triethylamine in 50 ml of acetonitrile, was added 50 mg (0.279 mmol) palladium (II) chloride, 147 mg (0.559 mmol) of triphenylphosphine, and 24 mg (0.126 mmol) of copper (I) iodide, under nitrogen. The resultant reaction mixture was allowed to react at reflux temperature for approximately thirty minutes. When the reaction was substantially complete, as indicated by TLC, the reaction mixture was cooled to room temperature and then filtered to provide a dark brown solid. This solid was washed with acetonitrile and dried in vacuo to provide 1.82 g of the desired compound.
Yield: 72%.
MS(FD): 452 (M).

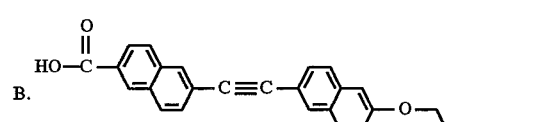

To a solution of 1.75 g (3.87 mmol) of the compound of Preparation 4A in 100 ml of a 4:1 tetrahydrofuran/water mixture, was added 370 mg (15.5 mmol) of lithium hydroxide. The resultant reaction mixture was reacted at room temperature for approximately nineteen hours. When the reaction was substantially complete, as indicated by TLC, the reaction mixture was acidified by the addition of 1E aqueous hydrochloric acid and then adding water which resulted in the formation of a precipitate. This precipitate was isolated by filtration and then dried in vacuo to provide 1.25 g of a grey solid.
Yield: 74%.
MS(FD):438 (M).

triphenylphosphine and 0.023 g (0.123 mmol) of copper (I) iodide in 50 ml of acetonitrile, under nitrogen.

Yield: 1.404 g (52%) of a black solid.
MS(FD): 478 (M).

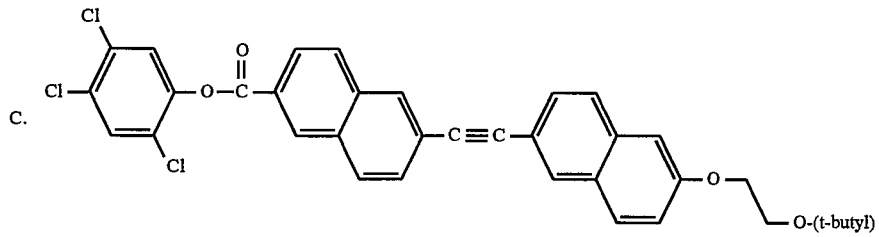

A solution containing 1.00 g (2.28 mmol) of the compound of Preparation 4B, 0.450 g (2.28 mmol) of 2,4,5-trichlorophenol and 0.470 (2.28 mmol) dicylcohexylcarbodiimde (DCC) in 100 ml of anhydrous methylene chloride was allowed to react overnight at room temperature. When the reaction was substantially complete, as indicated by

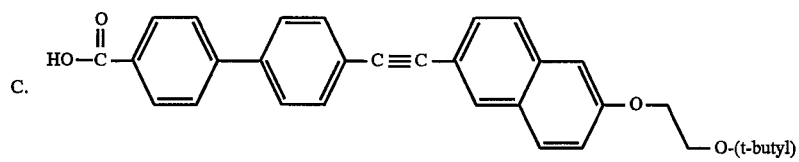

TLC, the reaction mixture was filtered. The filtrate was concentrated in vacuo to provide a residue. This residue was crystallized using a diethyl ether/pentane mixture and then dried in vacuo to provide a green solid.
Yield: 83%.
MS(FD): 616, 618 (M).

PREPARATION 5

A. 1-carbomethoxy-4'-trifluoromethylsulfonatebiphenyl

The desired compound was prepared substantially in accordance with the procedure detailed in Preparation 3A, using 16.00 g (70.10 mmol) of 1-carbomethoxy-4'-hydroxybiphenyl and 20.00 ml (70.89 mmol) of triflic anhydride [(CF$_3$SO$_2$)$_2$O] in 150 ml of anhydrous pyridine. The crude material was dissolved in methylene chloride, washed sequentially with water, a 1N hydrochloric acid solution, water, and brine, dried over sodium sulfate, filtered and then dried in vacuo to provide 21.92 g of a yellow solid.
Yield: 86.8%.
MS(FD): 360 (M).

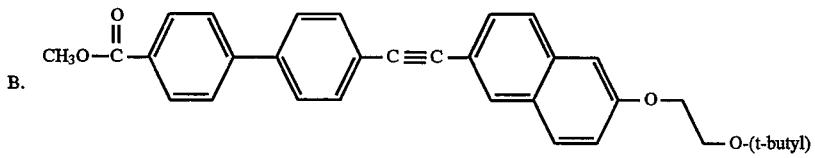

The desired compound was prepared substantially in accordance with the procedure detailed in Preparation 4A, using 1.50 g (5.59 mmol) of the compound of Preparation 3D, 2.014 g (5.590 mmol) of the compound of Preparation 5A, 1.56 ml (11.2 mmol) of triethylamine, 0.050 g (0.279 mmol) of palladium (II) chloride, 0.147 g (0.559 mmol) of The desired compound was prepared substantially in accordance with the procedure detailed in Preparation 4B, using 1.300 g (2.716 mmol) of the compound of Preparation 5B, 260 mg (10.86 mmol) of lithium hydroxide in 100 ml of a 1:4 water/tetrahydrofuran mixture.
Yield: 1.159 g (92%).
MS(FD): 465 (MH$^+$).

D. 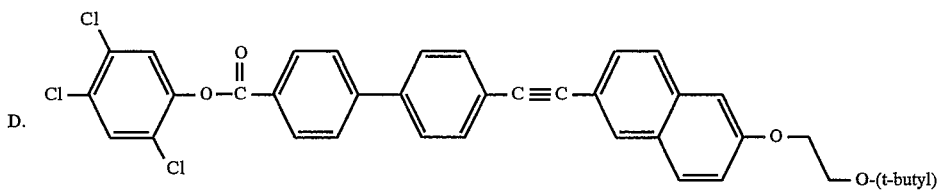

The desired compound was prepared substantially in accordance with the procedure detailed in Preparation 4C, using 1.00 g (2.15 mmol) of the compound of Preparation 5B 0.425 g (2.15 mmol) of 2,4,5-trichlorophenol and 0.444 g (2.15 mmol) of DCC in 200 ml of anhydrous methylene chloride.

Yield: 1.125 g (81%).

MS(FD): 644 (M).

EXAMPLE 1

Preparation of the compound of formula I where R', R" and R'" are each methyl, $R^{x1}$ is hydroxy, $R^{x2}$, $R^{y1}$, $R^{y2}$, $R^{y3}$, $R^{y4}$ and $R^o$ are each hydroxy, and

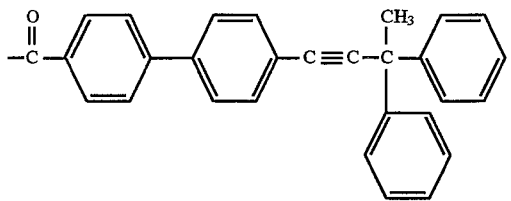

To a solution containing 195 mg (0.34 mmol) of the 2,4,5-trichlorophenol activated ester of the compound of Preparation 1G in 25 ml of dimethylformamide, was added 214 mg (0.27 mmol) of the (A-30912A) nucleus (compound of formula IB where R', R" and R'" are each methyl, $R^{x1}$ is hydroxy, $R^{x2}$, $R^{y1}$, $R^{y2}$, $R^{y3}$ and $R^{y4}$ are each hydroxy, and $R^o$ is hydroxy), under nitrogen. After stirring for approximately 5.5 days at room temperature, the reaction mixture was concentrated in vacuo to provide a residue. This residue was slurried in diethyl ether, sonicated and then isolated by filtration to provide a white solid. This solid was washed with methylene chloride resulting in the formation of a wax. This wax was purified using HPLC (eluent of 7:7.8:0.2 methylene chloride/methanol/water). The fractions containing the desired compound were combined and concentrated in vacuo to provide 132 mg of the desired compound.

Yield: 42%.

MS(FAB) for $C_{63}H_{72}N_7O_{16}$:

Calcd: 1182.5034 (MH+);

Found: 1182.5013.

EXAMPLE 2

Preparation of the compound of formula I where R', R" and R'" are each methyl, $R^{x1}$ is hydroxy, $R^{y2}$, $R^{y1}$, $R^{y2}$, $R^{y3}$, $R^{y4}$ and $R^o$ are each hydroxy, and $R^2$ is

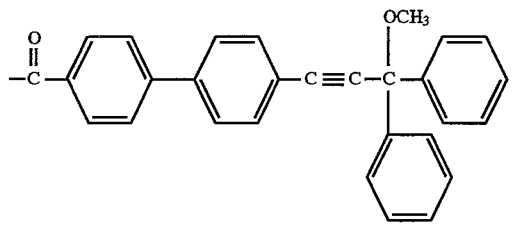

To a solution containing 1.21 g (2.02 mmol) of the 2,4,5-trichlorophenol activated ester of the compound of Preparation 2E in 100 ml of dimethylformamide, was added 1.29 g (1.6 mmol) of the (A-30912A) nucleus (compound of formula IB where R', R" and R'" are each methyl, $R^{x1}$ is hydroxy, $R^{x2}$, $R^{y1}$, $R^{y2}$, $R^{y3}$ and $RY^4$ are each hydroxy, and $R^o$ is hydroxy). After stirring for approximately three days at room temperature, the reaction mixture was concentrated in vacuo to provide a residue. This residue was slurried in diethyl ether and then isolated by filtration to provide a light yellow solid. This solid was dissolved with 10–20 ml of a methylene chloride/methanol mixture and then purified using HPLC (SiO$_2$; eluent of 10% aqueous acetonitrile; 1 ml/min.; 280 nm). The fractions containing the desired compound were combined and concentrated in vacuo to provide 1.25 g of the desired compound.

Yield: 52%.

MS(FAB) for $C_{63}H_{72}N_7O_{17}$:

Calcd: 1198.4985 (MH+);

Found: 1198.4984.

EXAMPLE 3

A. Preparation of the compound of formula I where R', R" and R'" are each methyl, $R^{x2}$, $R^{y1}$, $R^{y2}$, $R^{y3}$, $R^{y4}$ and $R^o$ are each hydroxy, $R^{x1}$ is prop-2-enyl and $R^2$ is

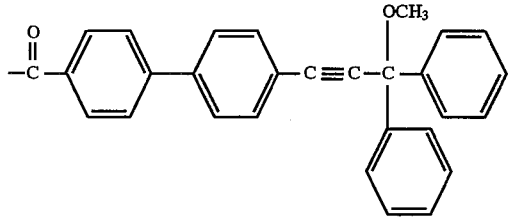

To an anhydrous solution containing 100 mg (0.0834 mmol) of the compound of Example 2 and 567 µl (8.34 mmol) of 3-hydroxypropene in 10 ml of anhydrous dioxane, was added approximately 2 mg of p-toluenesulfonic acid. When the reaction was substantially complete, as indicated by TLC, approximately 1 ml of a saturated sodium bicarbonate solution was added to the reaction mixture and the resultant mixture was stirred for approximately one hour and then concentrated in vacuo to provide a solid. This solid was suspended in water, filtered and washed with water. This solid was then removed from the funnel using methanol and the resulting mixture was purified using reverse phase preparative HPLC (eluent of 60% aqueous acetonitrile, 75 ml/min.; 290 nm) to provide the desired subtitled compound which was used without further purification.

B. Preparation of the compound of formula I where R', R" and R'" are each methyl, $R^{x2}$, $R^{y1}$, $R^{y1}$, $R^{y2}$, $R^{y3}$, $R^{y4}$ and $R^{0}$ are each hydroxy, $R^{x1}$ is 2,3-dihydroxypropyl and $R^2$ is

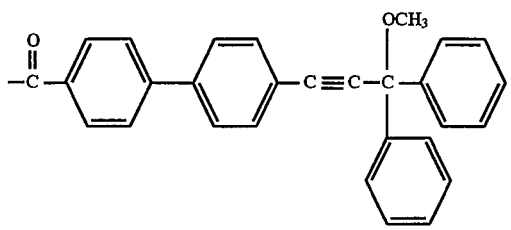

To a solution of the compound of Example 3A in a 1:1 mixture of dioxane and water, was added 4-methylmorpholine 4-oxide monohydrate (NMO) followed by osmium tetroxide. After stirring for 18–20 hours, sodium metabisulfite was added and 'the resultant mixture was allowed to react for approximately 3.5 hours. The liquid was decanted from the resultant mixture and then concentrated in vacuo to provide a residue. This residue was redissolved in methanol and then filtered through a fritted glass funnel. The filtrate was concentrated in vacuo, redissolved in a methanol/acetonitrile solution and then purified using reverse phase preparative HPLC (eluent of 50% aqueous acetonitrile, 75 ml/min.; 290 nm) to provide the desired subtitled compound.

MS(FAB) for $C_{66}H_{77}N_7O_{19}Li$:

Calcd: 1278.5434;

Found: 1278.5475

EXAMPLE 4

Preparation of the compound of formula I where R', R" and R'"are each methyl, $R^{x1}$ is hydroxy, $R^{x2}$, $R^{y1}$, $R^{y2}$, $R^{y3}$, $R^{y4}$ and $R^{0}$ are each hydroxy, and $R^2$ is

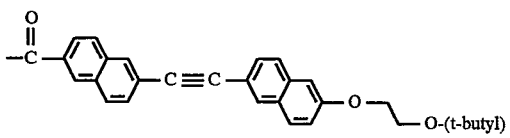

To a solution of 1.42 g (1.78 mmol) of the (A-30912A) nucleus (compound of formula IB where R', R" and R'" are each methyl, $R^{x1}$ is hydroxy, $R^{x2}$, $R^{y1}$, $R^{y2}$, $R^{y3}$ and $R^{y4}$ are each hydroxy and $R^{0}$ is hydroxy) in 200 ml of anhydrous dimethylformamide, was added 1.10 g (1.78 mmol) of the compound of Preparation 4C. When the reaction was substantially complete, as indicated by TLC, the reaction mixture was concentrated in vacuo to provide a residue. This residue was triturated in diethyl ether, isolated by filtration and then dried in vacuo to provide a grey solid. This solid was redissolved in 50 ml of methanol mixture. The resultant solution was diluted with 225 ml of water and then acidified to pH 4 by the addition off acetic acid which resulted in the formation of a precipitate. This solid was isolated by filtration, suspended in acetone and then filtered to removed the remaining solid. The filtrate was lyophilized from a dioxane/water mixture to provide 853 mg of a brown solid which was shown to be 96% pure using HPLC (eluent of 50% aqueous acetonitrile containing 1% trifluoroacetic acid; 1 ml/min.; 230 nm; RT=5.97 min.).

Yield: 39%.

MS(FAB) for $C_{63}H_{76}N_7O_{18}$:

Calcd: 1218.5247;

Found: 1218.5327.

EXAMPLE 5

Preparation of the compound of formula I where R', R" and R'" are each methyl, $R^{x1}$ is hydroxy, $R^{x2}$, $R^{y1}$, $R^{y2}$, $R^{y3}$, $R^{y4}$ and $R^{0}$ are each hydroxy, and $R^2$ is

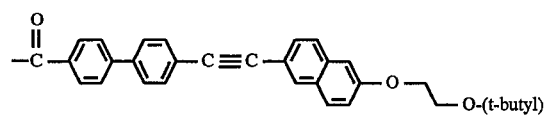

The desired compound was prepared substantially in accordance with the procedure detailed in Example 4, using 1.126 g (1.412 mmol) of the (A-30912A) nucleus (compound of formula IB where R', R" and R'" are each methyl, $R^{x1}$ is hydro, $R^{x2}$, $R^{y1}$, $R^{y2}$, $R^{y3}$ and $R^{y4}$ are each hydroxy, and $R^{0}$ is hydroxy) and 1.00 g (1.55 mmol) of the compound of Preparation 5D in 200 ml of dimethylformamide, with the exception that the reaction was allowed to react for approximately three days to provide a fluffy yellow solid which was determined to be 91.7% pure using HPLC (C18; eluent of 50% aqueous acetonitrile containing 0.1% trifluoroacetic acid; 2 ml/min.; 230 nm; $R_T$=8.48 min.).

Yield: 950 mg (54%).

MS (FAB) for $C_{65}H_{78}N_7O_{18}$:

Calcd: 1244.5403;

Found: 1244.5357.

The compounds of formula I exhibit antifungal and antiparasitic activity. For example, the compounds of formula I inhibit the growth of various infectious fungi including Candida spp. such as *C. albicans, C. parapsilosis, C. krusei, C. glabraca,* or *C. tropicalis, C. lusitaniae;* Torulopsis spp. such as *T. glabrata;* Aspergillus spp. such as *A. fumigatus;* Histoplasma spp. such as *H. capsulatum;* Cryptococcus spp. such as *C. neoformans;* Blastomyces spp. such as *B. dermatitidis;* Fusarium spp., Trichophyton spp., *Pseudallescheria boydii, Coccidioides immitis, Sporothrix schenckii* and the like.

Antifungal activity of a test compound was determined in vitro by obtaining the minimum inhibitory concentration (MIC) of the compound using a standard agar dilution test or a disc-diffusion test. The compound was then tested in vivo (in mice) to determine the effective dose of the test compound for controlling a systemic fungal infection.

Accordingly, the following compounds were tested for antifungal activity against *C. albicans.*

TABLE 1

| Minimal inhibitory concentration against *C. albicans* | |
| --- | --- |
| Example No. | MIC (µg/ml) |
| 1 | 0.039 |
| 2 | 0.156 |
| 3B | 0.156 |
| 4 | 0.005 |
| 5 | N.T. |

N.T. not tested

In addition, the effective dose of the following compounds for controlling a systemic fungal infection (*C. albicans*) was tested in vivo (mice).

TABLE 2

| $ED_{50}$ (mouse) | |
| --- | --- |
| Example No. | $ED_{50}$ (mg/kg) |
| 1 | N.T. |
| 2 | >50 |
| 3B | N.T. |
| 4 | 22 (oral) |
| 5 | N.T. |

N.T. not tested

The compounds of the invention also inhibit the growth of certain organisms primarily responsible for opportunistic infections in immunosuppressed individuals. For example the compounds of the invention inhibit the growth of *Pneumocystis carinii* the causative organism of pneumocystis pneumonia (PCP) in AIDS and other immunocompromised patients. Other protozoans that are inhibited by compounds of formula I include Plasmodium spp., Leishmania spp., Trypanosoma spp., Cryptosporidium spp., Isospora spp., Cyclospora spp., Trichomonas spp., Microsporidiosis spp. and the like.

The compounds of formula I are active in vitro and in vivo and are useful in combating either systemic fungal infections or fungal skin infections. Accordingly, the present invention provides a method of inhibiting fungal activity comprising contacting a compound of formula I, or a pharmaceutically acceptable salt thereof, with a fungus. A preferred method includes inhibiting *Candida albicans* or *Aspergillus fumigatis* activity. The present invention further provides a method of treating a fungal infection which comprises administering an effective amount of a compound of formula I, or a pharmaceutically acceptable salt thereof, to a host in need of such treatment. A preferred method includes treating a *Candida albicans* or *Aspergillus fumigatis* infection.

With respect to antifungal activity, the term "effective amount," means an amount of a compound of the present invention which is capable of inhibiting fungal activity. The dose administered will vary depending on such factors as the nature and severity of the infection, the age and general health of the host and the tolerance of the host to the antifungal agent. The particular dose regimen likewise may vary according to such factors and may be given in a single daily dose or in multiple doses during the day. The regimen may last from about 2–3 days to about 2–3 weeks or longer. A typical daily dose (administered in single or divided doses) will contain a dosage level of from about 0.01 mg/kg to about 100 mg/kg of body weight of an active compound of this invention. Preferred daily doses generally will be from about 0.1 mg/kg to about 60 mg/kg and ideally from about 2.5 mg/kg to about 40 mg/kg.

The present invention also provides pharmaceutical formulations useful for administering the antifungal compounds of the invention. Accordingly, the present invention also provides a pharmaceutical formulation comprising one or more pharmaceutically acceptable carriers, diluents or excipients and a compound of claim 1. The active ingredient in such formulations comprises from 0.1% to 99.9% by weight of the formulation, more generally from about 10% to about 30% by weight. By "pharmaceutically acceptable" it is meant that the carrier, diluent or excipient is compatible with the other ingredients of the formulation and not deleterious to the recipient thereof.

A compound of formula I may be administered parenterally, for example using intramuscular, subcutaneous, or intra-peritoneal injection, nasal, or oral means. In addition to these methods of administration, a compound of formula I may be applied topically for skin infections.

For parenteral administration the formulation comprises a compound of formula I and a physiologically acceptable diluent such as deionized water, physiological saline, 5% dextrose and other commonly used diluents. The formulation may contain a solubilizing agent such as a polyethylene glycol or polypropylene glycol or other known solubilizing agent. Such formulations may be made up in sterile vials containing the antifungal and excipient in a dry powder or lyophilized powder form. Prior to use, a physiologically acceptable diluent is added and the solution withdrawn via syringe for administration to the patient.

The present pharmaceutical formulations are prepared by known procedures using known and readily available ingredients. In making the compositions of the present invention, the active ingredient will generally be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10% by weight of the active compound, soft and hard gelatin capsules, suppositories, sterile injectable solutions, sterile packaged powders and the like.

For oral administration, the antifungal compound is filled into gelatin capsules or formed into tablets. Such tablets may also contain a binding agent, a dispersant or other suitable excipients suitable for preparing a proper size tablet for the dosage and particular antifungal compound of the formula I. For pediatric or geriatric use the antifungal compound may be formulated into a flavored liquid suspension, solution or emulsion. A preferred oral formulation is linoleic acid, cremophor RH-60 and water and preferably in the amount (by volume) of 8% linoleic acid, 5% cremophor RH-60, 87% sterile water and a compound of formula I in an amount of from about 2.5 to about 40 mg/ml.

For topical use the antifungal compound may be formulated with a dry powder for application to the skin surface or it may be formulated in a liquid formulation comprising a solubilizing aqueous liquid or non-aqueous liquid, e.g., an alcohol or glycol.

The following formulation examples are illustrative only and are not intended to limit the scope of the invention in any way. The term "active ingredient" means a compound according to formula I or a pharmaceutically acceptable salt thereof.

FORMULATION 1

Hard gelatin capsules are prepared using the following ingredients:

|                    | Quantity (mg/capsule) |
|--------------------|-----------------------|
| Active ingredient  | 250                   |
| Starch, dried      | 200                   |
| Magnesium stearate | 10                    |
| Total              | 460 mg                |

FORMULATION 2

A tablet is prepared using the ingredients below:

|                           | Quantity (mg/capsule) |
|---------------------------|-----------------------|
| Active ingredient         | 250                   |
| Cellulose, microcrystalline | 400                 |
| Silicon dioxide, fumed    | 10                    |
| Stearic acid              | 5                     |
| Total                     | 665 mg                |

The components are blended and compressed to form tablets each weighing 665 mg.

FORMULATION 3

An aerosol solution is prepared containing the following components:

|                       | Weight |
|-----------------------|--------|
| Active ingredient     | 0.25   |
| Methanol              | 25.75  |
| Propellant 22         | 74.00  |
| (Chlorodifluoromethane) |      |
| Total                 | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

FORMULATION 4

Tablets, each containing 60 mg of active ingredient, are made as follows:

|                                                 |         |
|-------------------------------------------------|---------|
| Active ingredient                               | 60 mg   |
| Starch                                          | 45 mg   |
| Microcrystalline cellulose                      | 35 mg   |
| Polyvinylpyrrolidone (as 10% solution in water) | 4 mg    |
| Sodium carboxymethyl starch                     | 4.5 mg  |
| Magnesium stearate                              | 0.5 mg  |
| Talc                                            | 1 mg    |
| Total                                           | 150 mg  |

The active ingredient, starch and cellulose are passed through a No. 45 mesh U.S. sieve and mixed thoroughly. The aqueous solution containing polyvinyl-pyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

FORMULATION 5

Capsules, each containing 80 mg of active ingredient, are made as follows:

|                              |        |
|------------------------------|--------|
| Active ingredient            | 80 mg  |
| Starch                       | 59 mg  |
| Microcrystalline cellulose   | 59 mg  |
| Magnesium stearate           | 2 mg   |
| Total                        | 200 mg |

The active ingredient, cellulose, starch and magnesium stearate are blended, passed through a No. 45 mesh U.S. sieve, and filled into hard gelatin capsules in 200 mg quantities.

FORMULATION 6

Suppositories, each containing 225 mg-of active ingredient, are made as follows:

|                               |          |
|-------------------------------|----------|
| Active ingredient             | 225 mg   |
| Saturated fatty acid glycerides | 2,000 mg |
| Total                         | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions, each containing 50 mg of active ingredient per 5 ml dose, are made as follows:

|                              |         |
|------------------------------|---------|
| Active ingredient            | 50 mg   |
| Sodium carboxymethyl cellulose | 50 mg |
| Syrup                        | 1.25 ml |
| Benzoic acid solution        | 0.10 ml |
| Flavor                       | q.v.    |
| Color                        | q.v.    |
| Purified water to total      | 5 ml    |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

FORMULATION 8

An intravenous formulation may be prepared as follows:

| Active ingredient | 100 mg |
|---|---|
| Isotonic saline | 1,000 ml |

The solution of the above ingredients generally is administered intravenously to a subject at a rate of 1 ml per minute.

The present invention further provides a method for treating or preventing the onset of Pneumocystis pneumonia in a host susceptible to Pneumocystis pneumonia which comprises administering an effective amount of a compound of formula I, or a pharmaceutically acceptable salt thereof, to a host in need of such treatment. The compounds of formula I can be used prophylactically to prevent the onset of the infection which is caused by the organism *Pneumocystis carinii*, or alternatively they can be used to treat a host that has been infected with *Pneumocystis carinii*. A compound of formula I may be administered parenterally, for example using intramuscular, intravenous or intraperitoneal injection, orally or by inhaling directly into the airways of the lungs. A preferred mode of administration is inhalation of an aerosol spray formulation of a compound of formula I.

With respect to antiparasitic activity, the term "effective amount," means an amount of a compound of the present invention which is capable of inhibiting parasitic activity. An effective amount of the compound of formula I is from about 3 mg/kg of patient body weight to about 100 mg/kg. The amount administered may be in a single daily dose or multiple doses of, for example, two, three or four times daily throughout the treatment regimen. The amount of the individual doses, the route of delivery, the frequency of dosing and the term of therapy will vary according to such factors as the intensity and extent of infection, the age and general health of the patient, the response of the patient to therapy and how well the patient tolerates the drug. It is known that Pneumocystis pneumonia infections in AIDS patients are highly refractory owing to the nature of the infection. For example, in severe, advanced infections the lumenal surface of the air passages becomes clogged with infectious matter and extensive parasite development occurs in lung tissue. A patient with an advanced infection will accordingly require higher doses for longer periods of time. In contrast, immune deficient patients who are not severely infected and who are susceptible to Pneumocystis pneumonia can be treated with lower and less frequent prophylactic doses.

We claim:
1. A compound of the formula:

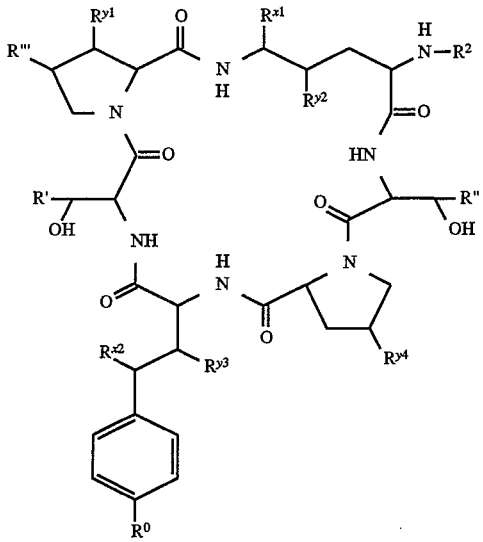

wherein:

R' is hydrogen, methyl or $NH_2C(O)CH_2$—;

R" and R'" are independently methyl or hydrogen;

$R^{x1}$ is hydrogen, hydroxy or —O—R;

R is $C_1$-$C_6$ alkyl, benzyl, —$(CH_2)_2Si(CH_3)_3$, —$CH_2CHOHCH_2OH$, —$CH_2CH=CH_2$, —$(CH_2)_aCOOH$, —$(CH_2)_bNR^{z1}R^{z2}$, —$(CH_2)_cPOR^{z3}R^{z4}$ or —$[(CH_2)_2O]_d$—($C_1$-$C_6$)alkyl;

a, b and c are independently 1, 2, 3, 4, 5 or 6;

$R^{z1}$ and $R^{z2}$ are independently hydrogen, $C_1$-$C_6$ alkyl, or $R^{z1}$ and $R^{z2}$ combine to form -$CH_2(CH_2)eCH_2$—;

$R^{z3}$ and $R^{z4}$ are independently hydroxy or $C_1$-$C_6$ alkoxy;

d is 1 or 2;

e is 1, 2 or 3;

$R^{x2}$, $R^{y1}$, $R^{y2}$, $R^{y3}$ and $R^{y4}$ are independently hydrogen or hydroxy;

$R^0$ is hydroxy, —$OP(O)(OH)_2$ or a group of the formulae:

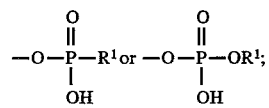

$R^1$ is $C_1$-$C_6$ alkyl, phenyl, p-halo-phenyl, p-nitrophenyl, benzyl, p-halo-benzyl or p-nitro-benzyl;

$R^2$ is

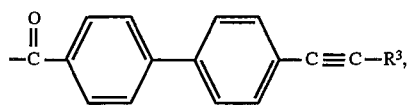

or

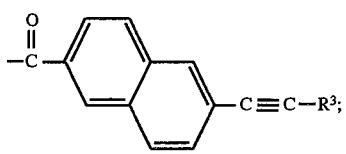

$R^3$ is

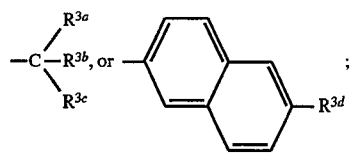

$R^{3a}$ is $C_1$-$C_6$ alkoxy;

$R^{3b}$ and $R^{3c}$ are independently phenyl or naphthyl;

$R^{3d}$ is $C_1$-$C_{12}$ alkyl, $C_1$-$C_{12}$ alkoxy or —O—$(CH_2)_m$—[O—$(CH_2)_n]_p$—O—($C_1$-$C_{12}$ alkyl);

m is 2, 3 or 4;

n is 2, 3 or 4; and p is 0 or 1;

or a pharmaceutically acceptable salt thereof.

2. A compound according to claim 1 where:

R', R" and R'" are each methyl;

$R^{y1}$, $R^{y2}$, $R^{y3}$ and $R^{y4}$ are each hydroxy;

$R^{x1}$ is hydrogen, hydroxy or —O—R;

R is methyl, benzyl, —$CH_2CHOHCH_2OH$, —$(CH_2)_b NR^{z1}R^{z2}$ or —$(CH_2)_2 POR^{z3}R^{z4}$;

b is 2, 3, 4, 5 or 6;

$R^{z1}$ and $R^{z2}$ are independently hydrogen, or $C_1$-$C_4$ alkyl;

$R^{z3}$ and $R^{z4}$ are independently hydroxy or methoxy;

$R^{x2}$ is hydrogen or hydroxy;

$R^o$ is hydroxy or a group of the formulae:

$$-O-\underset{\underset{OH}{|}}{\overset{\overset{O}{\|}}{P}}-R^1 \text{ or } -O-\underset{\underset{OH}{|}}{\overset{\overset{O}{\|}}{P}}-OR^1;$$

$R^1$ is methyl;

or a pharmaceutically acceptable salt thereof.

3. A compound according to claim 2 where:

$R^2$ is

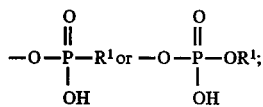

$R^3$ is

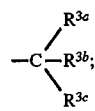

$R^{3a}$ is methyl or methoxy; and $R^{3b}$ and $R^{3c}$ are each phenyl;

or a pharmaceutically acceptable salt thereof.

4. A compound according to claim 2 where:

$R^2$ is

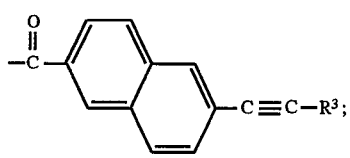

$R^3$ is

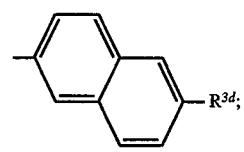

$R^{3d}$ is $C_1$-$C_{12}$ alkoxy or —O—$(CH_2)_m$—[O—$(CH_2)_n]_p$—O—($C_1$-$C_{12}$ alkyl);

m is 2;

n is 2; and p is 0 or 1;

or a pharmaceutically acceptable salt thereof.

5. The compound according to claim 3 where:

$R^{x1}$ is hydroxy;

$R^{x2}$ is hydroxy;

$R^o$ is hydroxy; and $R^{3a}$ is methyl;

or a pharmaceutically acceptable salt thereof.

6. The compound according to claim 4 which is $R^{x1}$ is hydroxy;

$R^{x2}$ is hydroxy;

$R^o$ is hydroxy; and $R^{3d}$ is —O—$(CH_2)_2$—O—(t-butyl);

or a pharmaceutically acceptable salt thereof.

7. A pharmaceutical formulation comprising one or more pharmaceutically acceptable carriers, diluents or excipients and a compound of claim 1.

8. A pharmaceutical formulation according to claim 7 wherein the compound is one where:

R', R" and R'" are each methyl;

$R^{y1}$, $R^{y2}$, $R^{y3}$ and $R^{y4}$ are each hydroxy;

$R^{x1}$ is hydrogen, hydroxy or —O—R;

R is methyl, benzyl, —$CH_2CHOHCH_2OH$, —$(CH_2)_b NR^{z1}R^{z2}$ or —$(CH_2)_2 POR^{z3}R^{z4}$;

b is 2, 3, 4, 5 or 6;

$R^{z1}$ and $R^{z2}$ are independently hydrogen, or $C_1$-$C_4$ alkyl;

$R^{z3}$ and $R^{z4}$ are independently hydroxy or methoxy;

$R^{x2}$ is hydrogen or hydroxy;

$R^o$ is hydroxy or a group of the formulae:

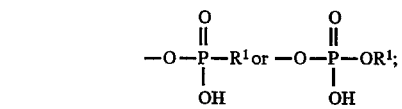

$R^1$ is methyl;

or a pharmaceutically acceptable salt thereof.

9. A pharmaceutical formulation according to claim 8 where the compound is one where:

R² is

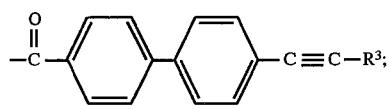

R³ is

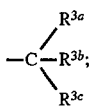

R$^{3a}$ is methyl or methoxy; and
R$^{3b}$ and R$^{3c}$ are each phenyl;
or a pharmaceutically acceptable salt thereof.

10. A pharmaceutical formulation according to claim 8 where the compound is one where:

R² is

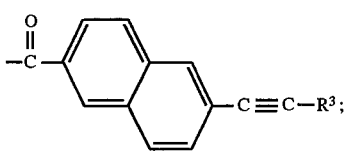

R³ is

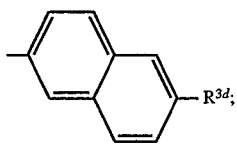

R$^{3d}$ is C$_1$-C$_{12}$ alkoxy or —O—(CH$_2$)$_m$—[O—(CH$_2$)$_n$]$_p$—O—(C$_1$-C$_{12}$ alkyl);
m is 2;
n is 2; and
p is 0 or 1;
or a pharmaceutically acceptable salt thereof.

11. The pharmaceutical formulation according to claim 9 where the compound is one where:
R$^{x1}$ is hydroxy;
R$^{x2}$ is hydroxy;
R$^o$ is hydroxy; and
R$^{3a}$ is methyl;
or a pharmaceutically acceptable salt thereof.

12. The pharmaceutical formulation according to claim 10 where the compound is one where:
R$^{x1}$ is hydroxy;
R$^{x2}$ is hydroxy;
R$^o$ is hydroxy; and
R$^{3d}$ is —O—(CH$_2$)$_2$—O—(t -butyl);
or a pharmaceutically acceptable salt thereof.

13. A method of inhibiting fungal activity comprising contacting a compound of claim 1 with a fungus.

14. A method according to claim 13 wherein the compound is one where:
R', R" and R'" are each methyl;
R$^{y1}$, R$^{y2}$, R$^{y3}$ and R$^{y4}$ are each hydroxy;
R$^{x1}$ is hydrogen, hydroxy or —O—R;

R is methyl, benzyl, —CH$_2$CHOHCH$_2$OH, —(CH$_2$)$_b$NR$^{z1}$R$^{z2}$ or —(CH$_2$)$_2$POR$^{z3}$R$^{z4}$;
b is 2,3,4,5 or 6;
R$^{z1}$ and R$^{z2}$ are independently hydrogen, or C$_1$-C$_4$ alkyl;
R$^{z3}$ and R$^{z4}$ are independently hydroxy or methoxy;
R$^{x2}$ is hydrogen or hydroxy;
R$^o$ is hydroxy or a group of the formulae:

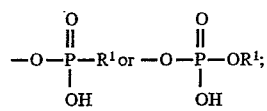

R¹ is methyl;
or a pharmaceutically acceptable salt thereof.

15. A method according to claim 14 where the compound is one where:
R² is

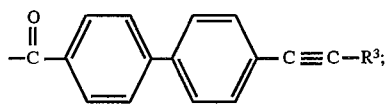

R³ is

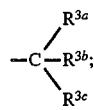

R$^{3a}$ is methyl or methoxy; and
R$^{3b}$ and R$^{3c}$ are each phenyl;
or a pharmaceutically acceptable salt thereof.

16. A method according to claim 14 where the compound is one where:
R² is

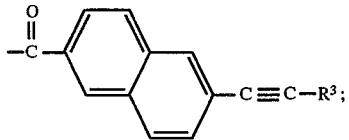

R³ is

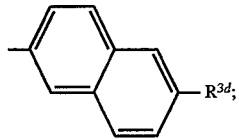

R$^{3d}$ is C$_1$-C$_{12}$ alkoxy or —O—(CH$_2$)$_m$—[O—(CH$_2$)$_n$]$_p$—O—(C$_1$-C$_{12}$ alkyl);
m is 2;
n is 2; and
p is 0 or 1;
or a pharmaceutically acceptable salt thereof.

17. The method according to claim 15 where the compound is one where:
R$^{x1}$ is hydroxy;
R$^{x2}$ is hydroxy;

R° is hydroxy; and

R³ᵃ is methyl;

or a pharmaceutically acceptable salt thereof.

18. The method according to claim 16 where the compound is one where:

R^{x1} is hydroxy;

R^{x2} is hydroxy;

R° is hydroxy; and

R³ᵈ is —O—(CH₂)₂—O—(t-butyl);

or a pharmaceutically acceptable salt thereof.

19. A method of treating a fungal infection which comprises administering an effective amount of a compound of claim 1 to a host in need of such treatment.

20. A method according to claim 19 wherein the compound is one where:

R', R" and R'" are each methyl;

R^{y1}, R^{y2}, R^{y3} and R^{y4} are each hydroxy;

R^{x1} is hydrogen, hydroxy or —O—R;

R is methyl, benzyl, —CH₂CHOHCH₂OH, —(CH₂)ᵦNR^{z1}R^{z2} or —(CH₂)₂POR^{z3}R^{z4};

b is 2, 3, 4, 5 or 6;

R^{z1} and R^{z2} are independently hydrogen, or C₁–C₄ alkyl;

R^{z3} and R^{z4} are independently hydroxy or methoxy;

R^{x2} is hydrogen or hydroxy;

R° is hydroxy or a group of the formulae:

$$-O-\overset{O}{\underset{OH}{P}}-R^1 \quad \text{or} \quad -O-\overset{O}{\underset{OH}{P}}-OR^1;$$

R¹ is methyl;

or a pharmaceutically acceptable salt thereof.

21. A method according to claim 20 where the compound is one where:

R² is

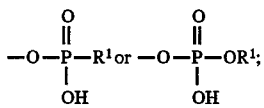

R³ is

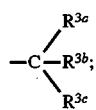

R³ᵃ is methyl or methoxy; and

R³ᵇ and R³ᶜ are each phenyl;

or a pharmaceutically acceptable salt thereof.

22. A method according to claim 20 where the compound is one where:

R² is

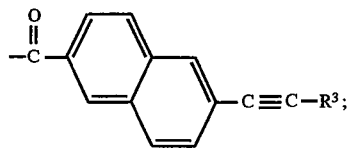

R³ is

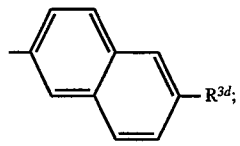

R³ᵈ is C₁–C₁₂ alkoxy or —O—(CH₂)ₘ—[O—(CH₂)ₙ]ₚ— O—(C₁–C₁₂ alkyl);

m is 2;

n is 2; and p is 0 or 1;

or a pharmaceutically acceptable salt thereof.

23. The method according to claim 21 where the compound is one where:

R^{x1} is hydroxy;

R^{x2} is hydroxy;

R° is hydroxy; and

R³ᵃ is methyl;

or a pharmaceutically accepmable salt thereof.

24. The method according to claim 22 where the compound is one where:

R^{x1} is hydroxy;

R^{x2} is hydroxy;

R° is hydroxy; and

R³ᵈ is —O—(CH₂)₂—O—(t-butyl);

or a pharmaceutically acceptable salt thereof.

25. A method for inhibiting parasitic activity comprising contacting a compound of claim 1 with a parasite.

26. A method according to claim 25 wherein the compound is one where:

R', R" and R'" are each methyl;

R^{y1}, R^{y2}, R^{y3} and R^{y4} are each hydroxy;

R^{x1} is hydrogen, hydroxy or —O—R;

R is methyl, benzyl, —CH₂CHOHCH₂OH, —(CH₂)ᵦNR^{z1}R^{z2} or —(CH₂)₂POR^{z3}R^{z4};

b is 2, 3, 4, 5 or 6;

R^{z1} and R^{z2} are independently hydrogen, or C₁–C₄ alkyl;

R^{z3} and R^{z4} are independently hydroxy or methoxy;

R^{x2} is hydrogen or hydroxy;

R° is hydroxy or a group of the formulae:

$$-O-\overset{O}{\underset{OH}{P}}-R^1 \quad \text{or} \quad -O-\overset{O}{\underset{OH}{P}}-OR^1;$$

R¹ is methyl;

or a pharmaceutically acceptable salt thereof.

27. A method according to claim 26 where the compound is one where:

$R^2$ is

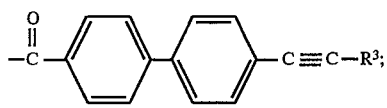

$R^3$ is

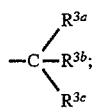

$R^{3a}$ is methyl or methoxy; and $R^{3b}$ and $R^{3c}$ are each phenyl;

or a pharmaceutically acceptable salt thereof.

28. A method according to claim 26 where the compound is one where:

$R^2$ is

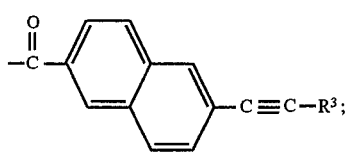

$R^3$ is

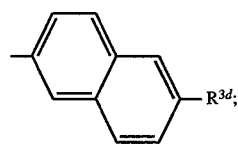

$R^{3d}$ is $C_1$-$C_{12}$ alkoxy or —O—$(CH_2)_m$—[O—$(CH_2)_n]_p$—O—($C_1$-$C_{12}$ alkyl);

m is 2;

n is 2; and p is 0 or 1;

or a pharmaceutically acceptable salt thereof.

29. The method according to claim 27 where the compound is one where:

$R^{x1}$ is hydroxy;

$R^{x2}$ is hydroxy;

$R^o$ is hydroxy; and $R^{3a}$ is methyl;

or a pharmaceutically acceptable salt thereof.

30. The method according to claim 28 where the compound is one where:

$R^{x1}$ is hydroxy;

$R^{x2}$ is hydroxy;

$R^o$ is hydroxy; and $R^{3d}$ is —O—$(CH_2)_2$—O—(t-butyl);

or a pharmaceutically acceptable salt thereof.

31. A method for treating or preventing the onset of Pneumocystis pneumonia in a host susceptible to Pneumocystis pneumonia which comprises administering an effective amount of a compound of formula I, or a pharmaceutically acceptable salt thereof, to a host in need of such treatment.

32. A method according to claim 31 wherein the compound is one where:

R', R" and R'" are each methyl;

$R^{y1}$, $R^{y2}$, $R^{y3}$ and $R^{y4}$ are each hydroxy;

$R^{x1}$ is hydrogen, hydroxy or —O—R;

R is methyl, benzyl, —$CH_2CHOHCH_2OH$, —$(CH_2)_bNR^{z1}R^{z2}$ or —$(CH_2)_2POR^{z3}R^{z4}$;

b is 2, 3, 4, 5 or 6;

$R^{z1}$ and $R^{z2}$ are independently hydrogen, or $C_1$-$C_4$ alkyl;

$R^{z3}$ and $R^{z4}$ are independently hydroxy or methoxy;

$R^{x2}$ is hydrogen or hydroxy;

$R^o$ is hydroxy or a group of the formulae:

$$-O-\overset{O}{\underset{OH}{P}}-R^1 \text{ or } -O-\overset{O}{\underset{OH}{P}}-OR^1;$$

$R^1$ is methyl;

or a pharmaceutically acceptable salt thereof.

33. A method according to claim 32 where the compound is one where:

$R^2$ is

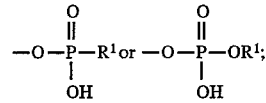

$R^3$ is

$R^{3a}$ is methyl or methoxy; and $R^{3b}$ and $R^{3c}$ are each phenyl;

or a pharmaceutically acceptable salt thereof.

34. A method according to claim 32 where the compound is one where:

$R^2$ is

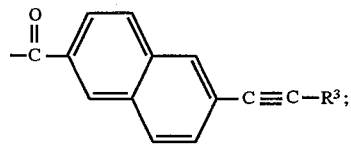

$R^3$ is

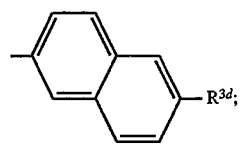

$R^{3d}$ is $C_1$-$C_{12}$ alkoxy or —O—$(CH_2)_m$—[O—$(CH_2)_n]_p$—O—($C_1$-$C_{12}$ alkyl);

m is 2;

n is 2; and p is 0 or 1;

or a pharmaceutically acceptable salt thereof.

35. The method according to claim 33 where the compound is one where:

$R^{x1}$ is hydroxy;
$R^{x2}$ is hydroxy;
$R^{o}$ is hydroxy; and
$R^{3a}$ is methyl;
or a pharmaceutically acceptable salt thereof.

36. The method according to claim 34 where the compound is one where:

$R^{x1}$ is hydroxy;
$R^{x2}$ is hydroxy;
$R^{o}$ is hydroxy; and
$R^{3d}$ is —O—$(CH_2)_2$—O—(t-butyl);
or a pharmaceutically acceptable salt thereof.

\* \* \* \* \*

UNITED STATES PATENT AND TRADEMARK OFFICE
CERTIFICATE OF CORRECTION

PATENT NO.   : 5,629,290

DATED        : May 13, 1997

INVENTOR(S)  : LaGrandeur, et al.

It is certified that an error appears in the above-identified patent and that said Letters Patent is hereby corrected as shown below:

Column 16, line 66, "1E" should read --1N--.

Column 19, line 30, " 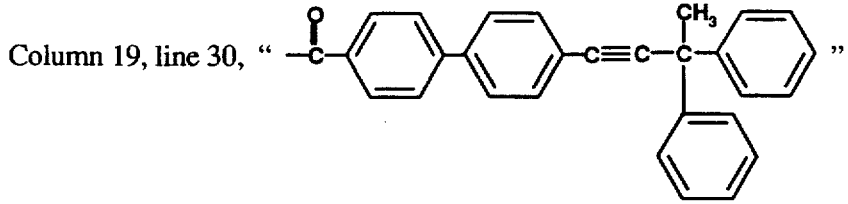 "

should read -- 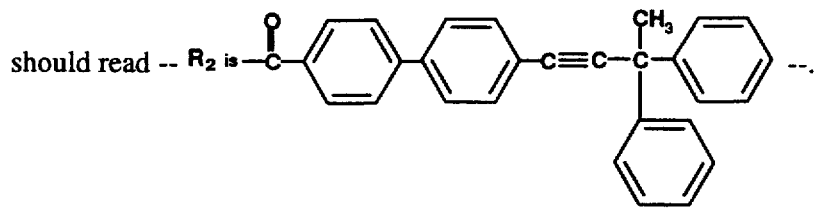 --.

Signed and Sealed this

Twentieth Day of October, 1998

Attest:

BRUCE LEHMAN

*Attesting Officer*  *Commissioner of Patents and Trademarks*